United States Patent [19]

Dellinger

[11] Patent Number: 4,551,096
[45] Date of Patent: Nov. 5, 1985

[54] ORTHODONTIC APPARATUS AND METHOD FOR TREATING MALOCCLUSION

[76] Inventor: Eugene L. Dellinger, 4606A E. State St., Fort Wayne, Ind. 46805

[21] Appl. No.: 662,727

[22] Filed: Oct. 19, 1984

Related U.S. Application Data

[63] Continuation-in-part of Ser. No. 562,858, Dec. 19, 1983.

[51] Int. Cl.⁴ ............................................... A61C 7/00
[52] U.S. Cl. ..................................................... 433/24
[58] Field of Search .................................. 433/24, 9, 3

[56] References Cited

U.S. PATENT DOCUMENTS

| | | | |
|---|---|---|---|
| 3,738,005 | 6/1973 | Cohen et al. | 433/24 |
| 3,949,477 | 4/1976 | Cohen et al. | 433/24 |
| 4,501,554 | 2/1985 | Hickham | 433/24 |

*Primary Examiner*—Robert Peshock
*Attorney, Agent, or Firm*—George A. Gust

[57] ABSTRACT

The invention comprehends the use of a fixture which fits over a tooth on which a bracket is to be affixed, this fixture having an internal cavity which matches the shape and contour of a portion of the tooth, such as lingual surface, incisal edge and a portion of the labial surface. A second portion of the labial or lingual side of the fixture is fixedly secured to the head portion of the bracket in such a manner as to align the surface of the base in the same anatomical plane or tooth surface as the labial or lingual surface. The fixture may be rigid and of a material which can be changed to a non-rigid state upon application of a state-changing medium thereto. A second fixture or appliance essentially like the fixture may be non-rigid or flexible and conformable over the fixture in such a manner as to be easily removed therefrom and from the bracket. Removal from the bracket is performed after the fixture with the bracket mounted therein is assembled to a tooth and the bracket is bonded thereto.

20 Claims, 9 Drawing Figures

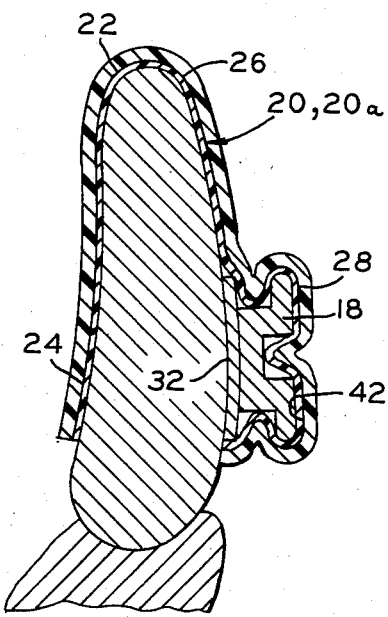
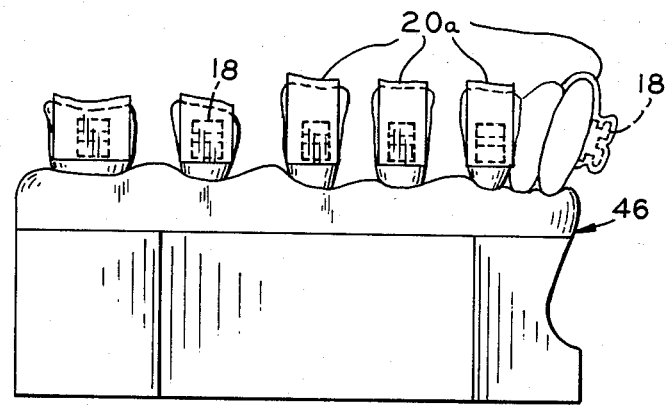
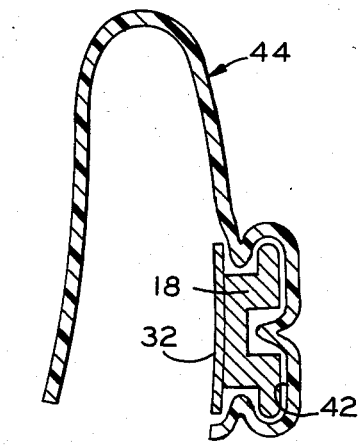
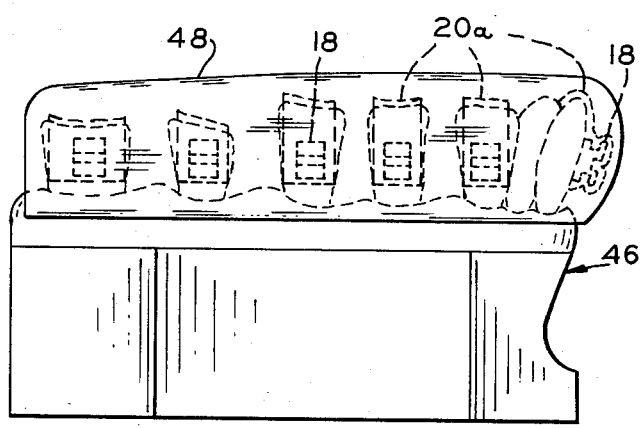
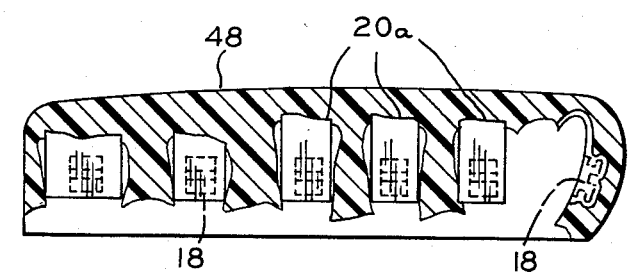

ORTHODONTIC APPARATUS AND METHOD FOR TREATING MALOCCLUSION

BACKGROUND OF THE INVENTION

1. Field of the Invention

This is a continuation-in-part of application Ser. No. 562,858, filed Dec. 19, 1983.

The present invention relates to orthodontics and more particularly to a method and apparatus useful in precisely locating a bracket on a patient's tooth in optimal position.

DESCRIPTION OF THE PRIOR ART

Prior art methods and apparatuses for precisely locating brackets on patient's teeth are disclosed in U.S. Pat. No. 3,738,005, 3,949,478, 4,014,096, 4,160,322, 4,183,141 and 4,360,341. Some of these patents disclose the use or procedures for the precise and correct placement of brackets upon the teeth utilizing idealized laboratory models. Brackets are mounted on the model in positions which conform to an idealized coplanar arch wire, while in others, prefabricated brackets are ideally located on the model and eventually incorporated into a transfer mask conforming to the malocclusion for placement on the patient's teeth. In still other of such patents, bracket-holding devices are incorporated into transfer masks adapted to be registered over patient's teeth. The bracket-holding devices or portions thereof serve in locating the brackets on the teeth in positions corresponding to those selected on the model. In Cohen et al U.S. Pat. No. 3,738,005, there is disclosed the forming of a bracket-retaining mold which is of flexible, self-sustaining, resilient character that has been molded into positive, capturing engagement with the brackets. In following this procedure, one of the first steps is to make a dental cast of the patient's malocclusion. Brackets are applied to the tooth replicas by the orthodontist in desired locations. A bracket-retaining mold is formed over the dental cast having the brackets mounted thereon. This results in providing an arch shaped transfer device which is then used to carry the brackets to the patient's mouth where the brackets are bonded into position. The flexible transfer device or positioner is then flexed off the brackets and teeth leaving the brackets in place.

In Schinhammer U.S. Pat. No. 3,949,478, the procedure is similar to that just described except an idealized model is fabricated and brackets are removably secured to the tooth replicas in coplanar position. These replicas with mounted brackets are then removed from the model and placed in a jaw model of the patient's malocclusion. There is then formed an arch shaped mold or transfer device of elastic material for carrying the brackets to the patient's mouth. Since this mold is elastic, it may be peeled or flexed off the patient's teeth and brackets the same as described above.

In the Dellinger U.S. Pat. No. 4,360,341, an arrangement similar to that of the foregoing two patents is disclosed to the extent of using a flexible fixture or transfer device for applying the brackets to the teeth in the patient's mouth.

SUMMARY OF THE INVENTION

The present invention relates to an apparatus and method by means of which brackets may be easily and precisely located and affixed to a patient's teeth in accordance with a fixed standard. This standard may be customized as to a particular patient or established by one of a series of typical case setups. This invention finds particular utility in a technique in which the slots of the brackets are predetermined on an idealized laboratory model, and are coplanar. When treatment of the patient is completed, the bracket slots are coplanar according to the slot arrangement on the idealized model. This generally corresponds to prior art methods and apparatuses.

In one method of this invention, the bracket is positioned on the patient's tooth precisely as predetermined according to the steps of forming a model for the patient's teeth in the shape of a dental arch with the replicas of the teeth ideally located. Brackets are releasably mounted on selected replicas in preselected locations. A fixture of a formable material is formed over the dental arch into intimate conformity with the crowns, the lingual and labial surfaces and onto the brackets in securing engagement therewith. The fixture is formed of a material which after being formed is relatively rigid but can be subsequently altered as to its physical properties to facilitate removal thereof from the brackets as well as the patient's teeth.

The replica configuration of the fixture is utilized to locate and bond the bracket onto the corresponding tooth in the patient's mouth. Once mounted, the physical properties of the utilized fixture are altered for facilitating removal thereof from the patient's teeth and the brackets.

In the specific embodiment of the foregoing arrangement, the material of the fixture is biodegradable and is intimately conformed about the head portion of the bracket, this material changing state into a non-rigid, flexible condition when subjected to moisture, which presents little resistance to the practitioner in picking it off the patient's tooth and bracket.

Further features of the invention reside in the use of an adhesive for securing releasably the brackets to the tooth replicas such that after the mold or fixture is formed over the replicas, the fixture and brackets as an integrated assembly can be bodily snapped or released from the replicas in such a manner that the portion of the adhesive contiguous with the tooth retains the precise surface contour thereof. When the bracket is transferred to the patient's tooth, that same exposed surface will then essentially precisely match the corresponding attachment area on the tooth.

In a modified embodiment, after forming the arch shaped fixture on the ideal model as explained in the foregoing, a second fixture, which for convenience, is referred to as a secondary appliance, is formed thereover in intimate conformity with the crown, lingual, labial and bracket surfaces and in engagement therewith. This appliance is also of a moldable material which can either be identical to that of the first fixture or in the alternative of a non-rigid flexible plastic. The appliance is removed from the fixture without damaging it preferably by merely flexing it over the protrusions presented by the head portions of the brackets with the result being an arch shaped tray or appliance having a cavitry conforming to the exterior shape of the idealized model with the fixture and brackets mounted thereon.

The appliance is then divided or sectioned into replica units which can be utilized individually to mount brackets in precise locations on the patient's teeth in precisely the same manner as the units formed on the primary fixture.

A still further alternative is to section the primary fixture into replica units after removing the fixture from the idealized model, these units having secured thereto the brackets over which they were initially formed. These bracket-retaining units are then applied to the corresponding replicas of a previously cast maloccluded model of the patient's teeth. Some or all of such replicas may have such units applied thereto. Over this model is then formed a secondary fixture or appliance as explained hereinabove which intimately conforms to the maloccluded arch with the primary fixture units and brackets thereon. The appliance may be secured to the fixture units either by means of a conventional, releasable adhesive or by reason of the physical embracement or encapsulation of the protruding bracket head portions of the first fixture. The appliance may then be manipulated to lift all of the fixture units with the retained brackets from the maloccluded model and transferring the same units directly to the patient's mouth where the brackets will be engaged with the surfaces of the corresponding teeth as on the maloccluded model. Conventional techniques at this point may be employed for the purpose of bonding the brackets directly to the teeth.

After the brackets have been secured, the appliance may be flexed off the teeth and fixture units and the fixture units then removed by altering the physical properties thereof as explained hereinabove. The brackets are thus bonded to the respective teeth in the identical locations as were first established on the ideal and maloccluded models.

Instead of forming the secondary appliance over the entire dental arch, it may be formed over only partial arches depending upon the treatment being followed by the practitioner.

It is an object of this invention to provide a method and apparatus which facilitates treatment of malocclusion.

It is another object of this invention to provide a method and apparatus for positioning brackets onto teeth with a high degree of precision.

The above-mentioned and the features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

In the drawings

FIG. 5 is a sectional view like that of FIG. 3 of the fixture unit with the bracket attached just prior to being transferred to a patient's tooth;

FIG. 6 is a sectional view like that of FIG. 5 but with the underlying fixture and dental cast or replica removed;

FIG. 7 is a side view like that of FIG. 1 of a maloccluded model of the teeth of a patient being treated with primary fixture units in place on replicas;

FIG. 8 is a view like that of FIG. 7 but with a secondary appliance formed over the arch with includes the replicas and primary fixture units; and FIG. 9 is a sectional view of the secondary appliance following its removal from the maloccluded model of FIGS. 7 and 8.

DESCRIPTION OF THE PREFERRED EMBODIMENT

Figure 1:
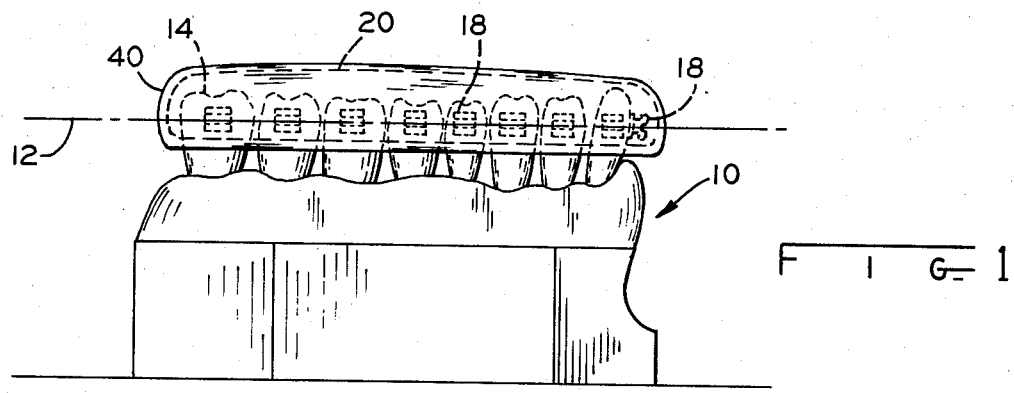
FIG. 1 is a side elevation of an idealized model of a dental arch illustrating one portion of the method of this invention.

In practicing the present invention, an idealized model of the patient's teeth is produced in accordance with conventional practice and otherwise as disclosed in Dellinger U.S. Pat. No. 4,014,096 and 4,360,341. A coplanar line or mark 12 is drawn on the tooth replicas 14. The line 12 on each replica 14 is utilized by the practitioner to select the desired location of the slot in a bracket to be directly bonded to the replica. The curvature of line 12 around the dental arch will correspond to the shape of an arch wire, preferably smoothly curvilinear and coplanar, to be used in the final stages of treatment. Other line patterns may be used without departing from the spirit and scope of this invention.

Suitable brackets 18 are bonded to the replicas 14 with the slots, for example, in registry with the line 12. While the bonding adhesive is conventional, it is of such character that it releasably mounts the brackets onto the replicas, adhering to the brackets more strongly than to the replicas. The adhesive in liquid or semi-liquid form is first applied to the attachment area on the labial or buccal surface of the replica, additional adhesive is provided on the mounting surface of the bracket base, following which the bracket is pressed onto the replica in the precise location desired for a short period of time until the adhesive cures to the point at which it retains the bracket in place. At this point, there will be excessive adhesive material which has flowed out from the edges of the bracket base, and this must be cleaned away. A suitably sharp instrument is used for the purpose, thereafter the adhesive is allowed to fully cure.

With the brackets so bonded to the replicas, a plastic cap or fixture 20 having the shape of the idealized model is formed over the replicas 14 and the brackets 18 mounted thereon. The fixture 20 intimately engages the incisal edges, the lingual surfaces and portions of the labial surfaces as indicated by the reference numerals 22, 24 and 26, respectively. The fixture thus has lingual, labial and incisal portions conforming to the surface anatomy of the corresponding portions of a patient's teeth. Further, the fixture 20 as molded over each bracket 18 (FIG. 3) intimately conforms to the undercuts and slots. This portion of the fixture 20, indicated by the numeral 28, appears as an embossment shaped substantially like the bracket-head portion. In the portion 28, the material substantially encapsulates and captures the bracket 18 in position.

In a working embodiment, in which the material of the fixture 20 is a thin, biodegradable film, a small amount of silicone adhesive is first applied to the outer surface of the bracket 18 for further adhering and locking the bracket 18 to the film.

The material of the fixture 20 preferably is plastic and may be in liquid, semi-liquid or solid film form. In a preferred arrangement, this material is a solidified biodegradable film which is heat moldable to be vacuum formed over the replicas and brackets. After being so formed, the material hardens. Once hardened, the fixture is for all practical purposes rigid, the antithesis of being flexible, resilient or elastic.

The fixture 20 and the encapsulated brackets 18 now constitute an integrated assembly which is releasably adhered to the model replicas. While still adhered, little handles 30 are attached by glueing or otherwise to the incisal edge portions of the fixtures in registry with each replica as shown in the drawings. After the various adhesives and materials have completely cured and hardened, the fixture-bracket assembly 18, 20 is merely withdrawn from the replicas simply by manually picking or forcing the brackets loose. Since the adhesive used in more releasable from the replica than it is in the bracket, the adhesive will separate from the replica leaving an imprint on the exposed surface of the adhesive area which intimately conforms to that of the attaching surface of the replica, hence the patient's tooth. This adhesive then becomes a part of the bracket and serves as a contoured shim whereby the bracket may be intimately fitted to the corresponding patient's teeth. Once removed, the fixture-bracket assembly 18, 20 appears as shown in FIG. 5 a (for a single tooth or replica and without the secondary overlay 40) with the exposed surface 32 of the bracket base serving as an anatomical extension of the inner surface of the labial portion 26 of the fixture 20. The fixture 20 is quite rigid, and once removed from the replica, it will having interior shapes corresponding to that of the respective replicas.

At this point it is necessary to make certain that the surface 32 on the bracket base is chemically clean. This is accomplished by blasting with an inert gas, such as nitrogen to an extent as will clean the surface for bonding to a patient's tooth.

Figure 4:
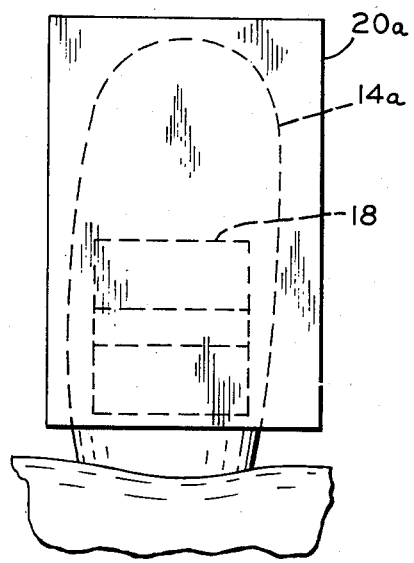
FIG. 4 is a labial view of the arrangement of FIG. 3.

The integrated arch-shaped fixture-bracket assembly 18, 20 is now sectioned into units, one for each replica 14. Each fixture unit 20a (see FIG. 4) may now be used to transfer a bracket 18 to the corresponding tooth 14a in the patient's mouth. The fixture 20a is now fitted over the corresponding tooth of the patient with the lingual, incisal and labial cavity portions fitting precisely, or in other words conforming to the surface anatomy of the corresponding shape and irregularities of the tooth. Since the bracket 18 is positively oriented with respect to the fixture unit 20a, the bracket 18 will be positioned on the patient's tooth in precisely the same position as it was on the replica.

Bonding of the bracket to the tooth is accomplished by applying cement to the tooth or bracket base before the fixture unit is applied to the tooth. The fixture unit 20a is held in position until the cement cures. Since the fixture unit 20a is quite rigid, once the fixture is applied to the tooth, the bracket 18 is automatically and precisely positioned with respect to the tooth. Stated in other words, since the fixture 20a is not flexible, resilient nor elastic the fitting of the fixture 20a over the tooth does not result in undesired movement laterally or otherwise of the bracket 18.

Since the material of the fixture 20a completely encircles and grips the bracket 18, and since the material is relatively rigid, it is, for all practical purposes, essentially non-removable from the bracket 18. However, the material of the fixture 20a is so selected that it can be altered in its physical properties from, for example rigid to non-rigid, rigid to flexible, reigid to soft, etc. By making the fixture of a film of biodegradable material, subjecting the fixture while mounted in the patient's mouth and after the bracket 18 has become bonded to the tooth, to moisture such as the saliva or a spray of water, the fixture tends to soften, become pliable or flexible following which it may be simply manually picked off the bracket and thereby removed from the patient's tooth. Brackets are applied to all of the patient's teeth in the same manner, there being an individualized unit 20a for each tooth.

The biodegradable film used in a working embodiment of this invention is essentially a flat, square sheet of thin film which is self-supporting. The material of the film is polyvinylalchohol, for example. In a working embodiment, it measure four inches on a side and is approximately eight to twelve mils thick. It may be used in conventional vacuum-forming equipment wherein heat is applied to the film at the time it is being vacuum formed over the replicas. Other materials may, of course, be used as long as the finished fixture is relatively rigid and can be altered in its physical properties from a rigid condition to one that is pliant, flexible or in other words non-rigid so that it may be conveniently and easily removed from the bracket once it has been mounted on the patient's tooth.

The individualized fixtures 20a are light in weight, diminutive, and non-bulky thereby facilitating manipulation for quick, easy, accurate installation. By being rigid the fixture enables direct bonding in a precise pre-selected position which, in utilizing the preferred technique described earlier, permits finished treatment by means of a pre-configured, coplanar archwire. Since the fixtures 20a are indivdualized, one for each tooth, they are individually useable irrespective of any anatomical changes as to other teeth. This is better understood by comparing with known positioners which are arch shaped to fit a patient's tooth malocclusion (See Cohen et at U.S. Pat. No. 3,738,005 and Shinhammer U.S. Pat. No. 3,949,478). Any change in any one tooth, for example, as to position, size, etc., renders the positioner unuseable since it no longer can fit the one tooth and simultaneously the remaining teeth.

Figure 2:
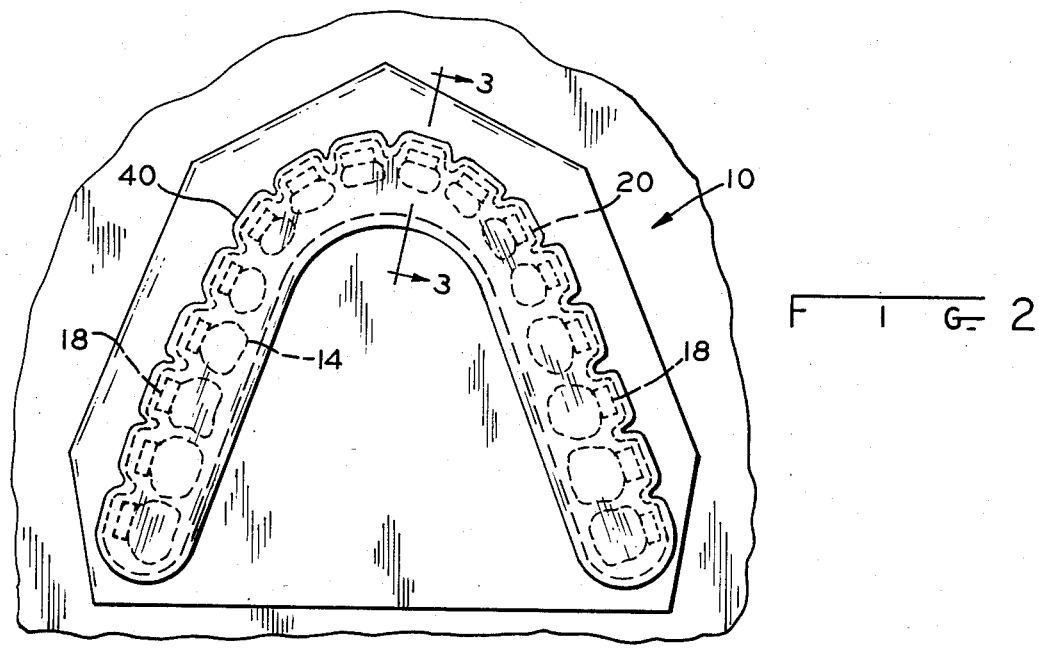
FIG. 2 is a top plan view thereof.

A variation or implementation of the foregoing method and apparatus is provided in accordance with the following. Referring to FIGS. 1 and 2, the primary fixture 20 is shown in dashed lines. Once this primary fixture 20 has been formed, a secondary occlusal fixture or overlay, also referred to as a secondary appliance, is formed thereover, as indicated by the numeral 40. The method and material employed may be identical to that disclosed hereinbefore, or in the alternative, a material which in the final analysis is suitably flexible, such as a type of vinyl plastic or the like. The method and materials used are such that the secondary appliance 40 can be physically separated from the fixture 20 simply by flexing the appliance 40 thereoff. If desired, a suitable releasable adhesive may be employed for securing both the fixture and appliance 20, 40 together for purposes of handling.

Figure 3:
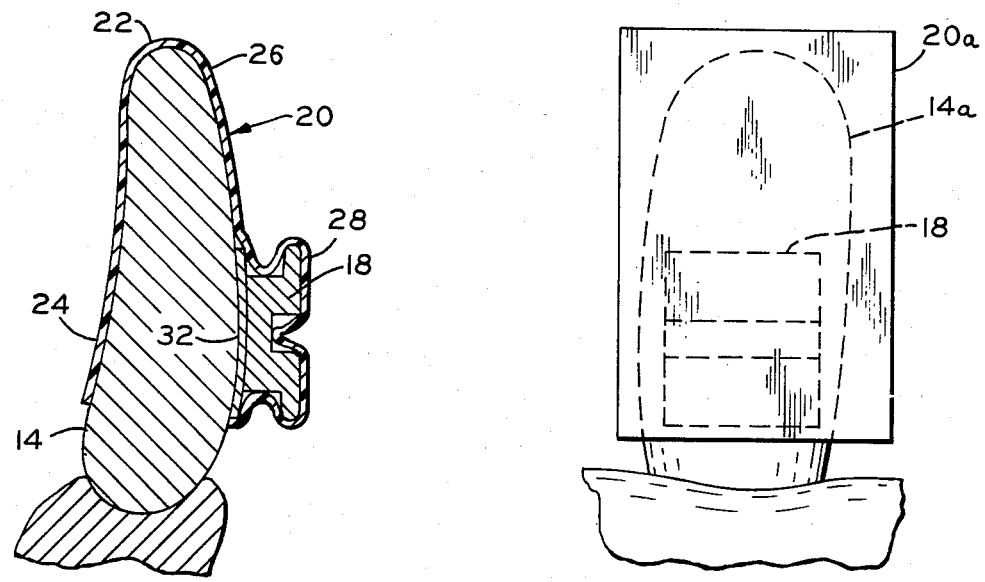
FIG. 3 is an enlarged sectional view taken substantially along section line 3—3 of FIG. 2.

Substantially in accordance with the method explained hereinbefore, the fixture-appliance assembly 18, 20, 40 is merely withdrawn from the model by manually picking or forcing the brackets loose. As removed, the fixture-appliance assembly 18, 20, 40 appears as shown in FIG. 5 (for a single tooth or replica) with all the other features remaining the same as already explained. At this point, the fixture-appliance 20, 40 as an assembly is sectioned into units, one for each replica 14. Alternatively, the appliance 40 can be peeled off the underlying fixture 20 then the appliance 40 sectioned into units. In vacuum forming or molding the appliance 40 in conformity with the external shape of the fixture-bracket 18, 20 assembly, the appliance will have formed therein sockets or cavities 42 having shapes corresponding to the embossments 28 (FIGS. 3 and 5). By making the material of the fixture 20 suitably thin, the cavity 42 can be made to correspond substantially to the shape of the head of the bracket as shown in FIG. 6, whereby a sectioned appliance unit 44 can have fitted thereinto and thereby captures a bracket 18 which now may be transferred directly to the patient's tooth according to the same procedure explained in the foregoing and using a fixture unit 20. This procedure would be exployed primarily for the purpose of replacing brackets which have for same reason become dislodged from the patient's tooth. After using the appliance unit 44 to rebond a bracket 18, the unit 44 can be reused in the future provided it is made from a material that is flexible and is not alterable in its physical properies from the mere application, for example, of moisture or saliva as in the case of the fixture 20.

An alternative to the method and apparatus just described, resides in forming a cast or model 46 of the patients's maloccluded teeth as illustrated in FIG. 7. Of course, the ideal model of FIGS. 1 and 2 can be formed in a conventional manner from such a maloccluded model. After forming the individual, fixture units 20a, these are placed on the corresponding replicas on the maloccluded model 46, the invidual fixture units being indicated by the numeral 20a. The other plastic tray or appliance 48 is formed or molded according to the same procedures previously described over the maloccluded model with the fixture units 20a mounted thereon. After the material of the newly molded part 48 has cured, it along with the fixture units 20a which are integrated or unitized therewith 20a, 48 are removed from the model 46 thereby providing a bracket-transfer appliance as illustrated in FIG. 9. This integrated appliance may then be used in accordance with the procedures conventionally known and disclosed, for example, in the Cohen et al and Shinhammer patents, supra. After the brackets 18 have been secured to the patient's teeth, the appliance 48 may be flexed off the fixture units 20a, and the latter then removed from the corresponding brackets by altering the physical properties thereof as explained previously. It is to be recalled that this composite appliance 20a, 48 utilizes the fixture units 20a of the material that can be altered as to its physical properties and is otherwise non-flexible or rigid, whereas the overlay or appliance 48 is formed of material which can be said to be non-rigid by comparison, or in other words is flexible.

It will now be understood that instead of fabricating the composite appliance 20, 48 of the entire dental arch, it may be formed as an incomplete or partial arch to overlay two or more teeth. The same technique may be employed to apply a bracket to a single tooth.

Since the bracket-locating fixtures of this invention are custom fabricated for the individual patient, free hand placement and many of the judgment factors involved on the part of practitioner are eliminated. Accuracy in bonding location coupled with a savings in practitioner's time can indeed provide for improved treatment at lower costs.

Summarizing, the invention broadly involves transporting the bracket to the mouth by means of a relatively rigid or non-rigid fixture or appliance, bonding the bracket in place, and then in the case of the rigid fixture altering the properties from rigid to flexible, to facilitate removal from the bracket. Ideal and maloccluded models of the patient's teeth may alternatively be used for making (1) duplicate transfer units for both initial and replacement installations on individual, single teeth of a patient and (2) arch-shaped appliances for precisely locating and installing simultaneously a plurality of brackets on patient's teeth.

While there have been described above the principles of this invention in connection with specific apparatus, it is to be clearly understood that this description is made only by way of example and not as a limitation to the scope of the invention.

What is claimed is:

1. The method of fabricating an orthodontic device for re-positioning a patient's teeth, comprising the steps of:
   forming a model of the patient's teeth in the shape of a dental arch with the replicas of the teeth ideally located,
   releaseably mounting brackets on selected replicas in preselected locations,
   forming a fixture over the dental arch in intimate conformity with the respective replica crowns, lingual and labial surfaces and onto said brackets in securing engagement with the latter, said fixture being formed of a material which after being formed is relatively rigid and in that state not readily removable from said brackets but can be subsequently altered as to its physical properties to facilitate removal from said brackets,
   dividing replica portions of said fixture into units, one for each selected replica, the units corresponding to said selected replicas having brackets secured therein, making a maloccluded model of the patient's teeth, fitting the bracket-bearing units over the corresponding replicas of the maloccluded model and then forming a secondary fixture-retaining and transferring appliance over the maloccluded model in intimate conformity therewith and in securing engagement with said bracket-bearing units, removing the secondary appliance and secured bracket-bearing units as an integrated assembly from the maloccluded model, applying said integrated appliance to the patient's teeth to locate and secure the brackets to the teeth, and removing the appliance and fixture units from the teeth including altering the physical properties of the units while in the patient's mouth for removal from the teeth.

2. The method of claim 1 including forming said appliance of a material which is flexible; said removing step including flexing said appliance as necesssary to remove it from said bracket-bearing units thereby leaving the latter in position on the patient's teeth, then removing said units by the aforesaid step of altering the physical properties thereof.

3. The method of claim 2 wherein said bracket-bearing units have an embossed portion overlying and corresponding to the shape of the retained brackets, the forming of said appliance including intimately conforming the same to said embossed portion thereby tending to lock said units thereto.

4. The method of claim 3 wherein the material of said fixture is biodegradable such that upon the application of moisture becomes less rigid and thereby removable from said brackets and teeth.

5. The method of claim 1 wherein the steps of forming said fixture and appliance includes the vacuum forming of relatively thin sheets of material onto the respective models.

6. The method of claim 1 including forming said appliance of a material having substantially the same properties as those of said units.

7. The method of claim 6 wherein the step of removing the appliance and units from the patient's teeth include altering the physical properties of both said appliance and units.

8. The method of claim 6 wherein the material of both said units and appliance is biodegradable.

9. Apparatus for positioning brackets onto a patient's teeth comprising a locating fixture having an internal cavity provided with lingual and labial sides and an incisal edge portion therebetween; said lingual side, incisal edge portion and of said labial side conforming to the surface anatomy of the corresponding portions of a selected patient's tooth, a bracket having head and base portions, a first portion of either said labial or lingual side fixedly embracing the head portion of said bracket in such position as to orient said base portion in substantially the same anatomical surface as the respective labial or lingual side, said fixture further being relatively rigid and further of a material which can be changed in physical properties upon application of a property-changing medium thereto, said fixture being of relatively thin sheet-like material of substantially uniform thickness, the outer surface of the side of the fixture embracing said bracket substantially conforming to the shape of the inner surface thereof whereby an embossment is provided which conforms substantially to the shape of said head portion, and a secondary transfer appliance of sheet-like material overlying said fixture and bracket in intimate conformity therewith and having a cavity portion which receives said embossment and said cavity being of a size and shape to engage and retain said head portion of said bracket.

10. The apparatus of claim 9 wherein said appliance is self-supporting and flexible whereby it may be deformed for removal from said fixture and embossment.

11. The apparatus of claim 9 wherein said appliance is formed of material having substantially the same physical properties as said fixture.

12. The apparatus of claim 11 wherein said fixture and appliance are of biodegradable material.

13. Apparatus for positioning brackets onto a patient's teeth comprising a plurality of individual locating fixtures having internal cavities provided with lingual and labial sides and incisal edge portions, respectively, said lingual sides, incisal edge portions and labial sides, respectively, conforming to the surface anatominies of the corresponding portions of selected ones of the patient's teeth, a plurality of brackets each having head and base portions, portions of either said labial or lingual sides fixedly embracing the head portions of said brackets in such positions as to orient said base portions in substantially the same anatomical surfaces as the respective labial or lingual sides, respectively, said fixtures being relatively rigid and further of a material which can be changed in physical properties upon application of a property-changing medium thereto, and a fixture-integrating and retaining appliance having internal cavities arranged and conforming to the patient's malocclusion with said fixtures and brackets fitted onto said selected teeth thereof, said appliance being removably secured to and integrating said fixtures, in place, whereby said appliance with said fixtures secured in place may be conformably engaged with the patient's teeth thereby selectively locating said onto the selected teeth in the patient's mouth.

14. The apparatus of claim 13 wherein
the one of said lingual or labial sides of said fixtures which embraces the respective bracket head portions is relatively thin and of uniform thickness, the portion of said one side which overlies the respective head portion constituting an embossment of conforming shape, said appliance being of a flexible material and having cavities which removably capture said embossments, respectively, thereby contributing to the securement and integration of said fixtures to said appliance.

15. The apparatus of claim 13 wherein the one of said lingual or labial sides of said fixture which embraces the respective bracket head portions is relatively thin and of uniform thickness, the portion of said one side which overlies the respective head portion constituting an embossment of conforming shape, said appliance being of a material having properties substantially like the material of said fixtures and having cavities which removably capture said embossments, respectively, thereby contributing to the securement of said fixtures to said appliance.

16. The apparatus of claim 15 wherein the material of said fixtures and appliance is biodegradable.

17. The method of fabricating an orthodontic device for re-positioning a patient's teeth, comprising the steps of:

forming a model of the patient's teeth in the shape of a dental arch with the replicas of the teeth ideally located, releaseably mounting brackets on selected replicas in preselected locations, forming a fixture over the dental arch in intimate conformity with the respective replica crowns, lingual and labial surfaces and onto said brackets in securing engagement with the latter, said fixture being formed of a material which after being formed is relatively rigid and in that state not readily removable from said brackets but can be subsequently altered as to its physical properties to facilitate removal thereof from said brackets, said fixture being relatively thin and of a substantially uniform thickness, the portions thereof overlying the head portions of said brackets thereby being in the form of embossments conforming to the shapes of the head portions, respectively, forming a secondary appliance over said model with said fixtures in place on the selected replicas into intimate conformity therewith and incapturing engagement with said embossments, dividing replica portions of said appliance into units, one of each fixture mounted replica, each unit thereby having a cavity conforming to the lingual, labial, incisal and embossment portions of the respective fixture mounted replica, the embossment cavity portion being formed to a size and shape as will position and retain the head portion of the corresponding bracket in essentially the same relative position as that on the corresponding replica, whereby each unit can be used to locate and bond the respective bracket onto the corresponding tooth in the patient's mouth.

18. The method of claim 17 wherein said fixture is divided in the same manner as said appliance to provide bracket-carrying units, and utilizing said bracket-carrying units to located and bond respective brackets onto the corresponding teeth in a patient's mouth.

19. The method of claim 17 wherein said appliance is formed of flexible material, and including the step of releaseably adhering each bracket into its respective embossment cavity.

20. The method of claim 17 wherein both said fixture and appliance are formed of biodegradable material.

* * * * *